(12) United States Patent
Min et al.

(10) Patent No.: US 6,817,971 B2
(45) Date of Patent: Nov. 16, 2004

(54) CARDIOPULMONARY LIFE SUPPORT SYSTEM

(75) Inventors: Byoung G. Min, Seoul (KR); Yong S. Won, Seoul (KR); Kyung Sun, Seoul (KR); Kwang J. Baek, Seoul (KR); Hyuk S. Lee, Seoul (KR); Yang R. Roh, Gunsan-si (KR); Chang M. Hwang, Seoul (KR); Jung C. Lee, Daegu-si (KR); Whang J. Lee, Suwon-si (KR)

(73) Assignee: Newheartbio Co., LTD, Anyang (KR)

( * ) Notice: Subject to any disclaimer, the term of this patent is extended or adjusted under 35 U.S.C. 154(b) by 470 days.

(21) Appl. No.: 10/005,537

(22) Filed: Dec. 7, 2001

(65) Prior Publication Data

US 2003/0060675 A1 Mar. 27, 2003

(30) Foreign Application Priority Data

Sep. 25, 2001  (KR) .................................... 2001-0059410

(51) Int. Cl.⁷ ............................................. A61N 1/362
(52) U.S. Cl. ....................................................... 600/16
(58) Field of Search ............................... 604/4.01, 5.01, 604/6.14–6.16, 8, 9, 19–28, 6.01, 99.03, 619; 600/16–18; 417/476–478, 477.5, 477.8, 477.12

(56) References Cited

U.S. PATENT DOCUMENTS 4,767,289 A * 8/1988 Parrott et al. .......... 417/477.12

FOREIGN PATENT DOCUMENTS

KR        1020000032507        9/2001

* cited by examiner

*Primary Examiner*—George Manuel
(74) *Attorney, Agent, or Firm*—Park & Sutton LLP; John K. Park

(57) ABSTRACT

A cardiopulmonary life support system is disclosed. The life support system comprises a housing defined by a top side, a bottom side, and an inner periphery. First and second tubes are adjacent to each other in the housing, and the first and second tubes each have an input port and an output port. An alternating member is attached to the housing and disposed between the first and second tubes. The alternating member alternately squeezes the first and second tubes.

21 Claims, 16 Drawing Sheets

CARDIOPULMONARY LIFE SUPPORT SYSTEM

CLAIMING FOREIGN PRIORITY

The applicant claims and requests a foreign priority, through the Paris Convention for the Protection of Industry Property, based on a utility model application filed in the Republic of Korea (South Korea) with the filing date of Sep. 25, 2001, with the utility model application number 10-2000-0032507, by the applicant. (See the attached declaration)

BACKGROUND OF THE INVENTION

The invention relates to an artificial heart for a patient requiring a cardiopulmonary life support in form of either artificial heart implantation or extracorporeal heart assistance. More specifically, the present invention relates to a cardiopulmonary life support system that substantially prevents blood clotting (thrombus) and dissolution or destruction of red blood cells (hemolysis) from occurring in blood vessels of a heart patient who receives its assistance.

FIG. 1 is a schematic view showing a heart 2, lungs 4 and a blood circulation in a mammal or a human, wherein arrows indicate direction of the blood circulation. As shown therein, the heart 2 includes two atriums above and two ventricles below. A main vein 6 is connected to the right atrium and the right ventricle is linked to a pulmonary artery 8. The lungs are connected to the left atrium and the left ventricle is linked to an aorta 10. Regular pumping of the left ventricle pushes out blood therein into the aorta 10 to deliver nutrition and oxygen to each capillary vessel in the body. Meanwhile, the blood with less oxygen is in turn collected in the main vein that links to the right atrium to complete a blood circulation known as a systematic circulation. The oxygen-depleted blood collected in the right atrium is released down to the right ventricle and sent to each lung through the pulmonary artery for blood oxygenation. The blood oxygenated in the lungs is released through the left atrium down to the left ventricle. Through the blood circulation for blood oxygenation also known as a pulmonary circulation, the oxygen-depleted blood is converted to an oxygen-rich blood and collected back in the left ventricle. The oxygen-rich blood collected in the left ventricle repeats the systematic circulation in accordance with the regular pumping which generates rhythmic pulses. A valve in each atrium and ventricle serves to prevent a reverse stream.

Each rhythmic pulse in the atriums and ventricles differs depending on age, sex and physical condition. However, the heart pulse frequency for an individual is regular in a stabilized condition. A standard per-minute heart pulse frequency is known to range about 100 to 140 for infants, 80 to 90 for elementary school kids, 60 to 80 for young and middle aged adults, and 60 to 70 for senior people. Male tends to be less in pulse frequency than female. In general, the smaller the body, the more frequent becomes the heart pulsation for animals. If the body-surface area is larger than the body volume, heat emission becomes further invigorated and thus blood circulation should be faster to complement the loss resulting from the heat emission. For example, the per-minute pulse frequency ranges about 30 to 40 for elephants, 90 to 90 for dogs, 140 to 160 for rabbits, and 200 to 300 for rats. The pulse frequency in an artificial heart can be adjusted by controlling the rotation of a motor that drives the artificial heart.

The heart along with lungs is the most crucial organ that allows a living body to maintain its life. However, the heart should remain motionless and emptied in order to conduct a precise surgical heart operation. Therefore, considering the vitality of the heart without which the life does not last more than five minutes, an artificial heart or cardiopulmonary assistance device should be inevitably utilized in such life threatening urgent circumstances as a heart attack, a sepsis related shock, or a myocardium infraction.

Many studies on artificial hearts have been focused on blood pumping which most affects functioning of an artificial heart in a body. The leading conventional arts regarding artificial hearts will be now briefly described focusing each function of blood pumping.

FIG. 2 is a view showing a conventional cardiopulmonary device using a rotary pump. As shown therein the rotary pumping device includes a blood storage, a rotary type pump 12, an oxygenator 13, and a flexible tube 14. The blood storage 11 stores therein a blood from a main vein of a patient. The rotary blood pump 12 serves to transfer the blood from the storage 11 to the oxygenator 13. The flexible tube 14 links the blood storage 12 and the oxygenator 13. The flexible blood tube 14 is arc-bent by 90 degrees around the rotary blood pump 12. A rotation shaft 15 is radially formed from the arc-bent portion of the tube 14 through the center of the rotary pump 12. A rotation arm 16 is engaged to the rotation shaft 15 and two rotary rollers 17 are rotatably provided to rotate in accordance with the rotation shaft 15. The rotation of the shaft 15 allows the pump 12 to serve to make a sequential squeezing rotation along the arc-bent portion of the tube 14. However, the squeezing rotation of the pump 12 fails to generate a stable, pulsatile blood pumping. Further, the excessive pressure for the squeezing rotation tends to easily lead to thrombosis and hemolysis in the oxygenator 13. Also, the rotary pump 12 is only usable for about 6 to 8 hours which substantially limits its application to a time taking surgical heart operation.

FIG. 3 shows a schematic cross-sectional view of a conventional centrifugal blood pump 21. The centrifugal blood pump 21 includes an input port (not shown) to receive blood from a flexible tube (not shown) connected to a right atrium, an output port 22 to release the blood from the blood pump 21, and an impeller 23 having blades. The rotation speed of the impeller 23 can be adjusted depending on a patient. However, since the blood in the centrifugal blood pump 21 becomes in contact with either the inner surface of the blood bump 21 or mechanical surfaces of the impeller 23, there may easily occur blood clotting or blood dissolution.

In particular, the damage incurrence on red blood cells or blood platelets due to the blood clotting and dissolution is determined by stress resulting from the blood flow in the pump 21 and by how long the blood has stayed in the pump 21. Also, the stress due to the blood flow is determined by the rotation speed of the impeller 23 and by the asperity of the mechanical surfaces, thereby increasing possibility of blood damage. The time period in which the blood stays in the centrifugal blood pump 21 is a major factor to consider in the pump design. A shear stress sufficient to affect the blood staying in the pump may lead to thrombosis resulting from congelation, embolism or fibrin accumulation on the inner surface of the pump. There may also occur blood dissolution or red cell destruction due to a flow separation, a cavitation, or a solution swirl which may be caused by the rotation of the impeller 22. Therefore, the centrifugal blood pump 21 can be utilized for a limited time period like the rotary blood pump.

FIG. 4 shows a conventional pulsatile blood pump 31. As shown therein, the pulsatile pump 31 includes a bag tube 32, a pressure plate 33, a plate support 34, a rotation body 35, and a drive motor 36. The bag tube 32 is provided with a valve (not shown) at each end thereof. The pressure plate 33 pressurizes the tube 32 for blood transfer. The plate support 34 supports and vertically shuttles the pressure plate 33. The rotation body 35 is threaded to allow the plate support 34 to make a vertical reciprocal movement.

When the pressure plate 33 the plate support 34 are lowered according to the rotation body 35 driven by the motor 36, the blood is discharged from the tube 32, and when raised the blood is supplied into the tube 32, thereby enabling the pulsatile blood pumping. However, the pulsatile blood pump 31 may cause friction by the contact of the rotation body and the plate support 34 to thereby undermine a stabilized reciprocal movement. Further, the reciprocal rotation of the drive motor 36 that drives the rotation body 35 may increase pressure for pumping the blood to the oxygenator, thereby incurring thrombosis and hemolysis.

FIG. 5 shows a conventional dual pulsatile blood pump 41. As shown therein, the pulsatile pump 41 includes input ports 43, 43', output ports 44, 44', input valves 45, 45', and output valves 46, 46'. Each valve is formed in a corresponding one of the ports. The pump 41 also includes a pump case 42 that houses therein a spherical body 52. The spherical body 52 has a groove 50 therearound and a gear 51. The gear 51 is engaged to a rack 53 attached to an inner wall of the pump case 42. A rubber membrane 49, 49' covers the gear 51, rack 53 and the groove 50. A belt 54 is carried in along the groove 50 of the body 52 and around a pulley 57 linked to a motor 56. A tension applied to the pulley 57 together with the engagement of the gear 51 and the rack 53 enables a shuttling movement of the spherical body 52, whereby the body 52 makes a horizontal shuttle movement to pump the blood in the blood chamber 48. The dual pulsatile blood pump 31 substantially decreases thrombosis and hemolysis compared to the rotary pump or other pulsatile pumps. However, the mechanical surfaces are exposed to the blood except for the rubber membranes 49, 49' and the input and output ports are also exposed to mechanical surfaces, which may still incur thrombosis and hemolysis. Further, the streamline formation around the input and output ports in the pump chamber 48, 48' may lead to pressure loss which easily results in blood clotting or blood dissolution. In addition, the continued friction and stress may serve to elongate the belt and this makes it difficult to maintain stable pulsation and blood pressure. Also, the conventional dual pulsatile blood pump 41 substantially increases production cost due to mechanical requirements for the shuttle movement of the spherical body 41.

SUMMARY OF THE INVENTION

The invention is contrived to overcome the conventional disadvantages. Accordingly, an object of the present invention is to provide a cardiopulmonary life support system that substantially prevents blood clotting (thrombosis) and dissolution or destruction of red blood cells (hemolysis) from occurring in blood vessels of a heart patient who receives its assistance.

Another object of the invention is to enable a heart patient to use the life support system for a longer time period in form of either extracorporeal life support or surgical implantation. A further object is to improve portability for an extracorporeal system application and to minimize the size of the life support system to facilitate implantation. A still further object is to realize a rhythmic pulsation substantially equivalent to the systematic pulsation in a living body.

To achieve the above-described objects, the cardiopulmonary life support system according to the present invention comprises a housing defined by a top side, a bottom, a rear side, and an inner periphery. First and second tubes are adjacent to each other in the housing, and the first and second tubes each have an input port and an output port. An alternating member is attached to the housing and disposed between the first and second tubes. The alternating member alternately squeezes the first and second tubes.

In an embodiment, the life support system further comprises a valve formed in said each input and output port to prevent a reverse stream in the first and second tubes, and an oxygenator connected to the output port of the first tube and the input port of the second tube to convert an oxygen-depleted blood to an oxygen-rich blood.

For a better performance, there may be further provided first and second blood storages. The first blood storage is formed between the oxygenator and the input port of the first tube to temporarily store therein the oxygen-rich blood oxygenated in the oxygenator. The second blood storage is connected to the output port of the second tube to temporarily store therein the oxygen-depleted blood.

In this construction, an initial squeezing of the alternating member on the first tube enables the oxygen-rich blood to partially pump out from the first tube through the first tube output port. A subsequent squeezing of the alternating member on the second tube enables the oxygen-depleted blood to partially pump out from the second tube through the second output port while a restoration of the first tube to its original shape enables the first tube to suck in as much as pumped out therefrom through the first input port valve. A further subsequent squeezing of the alternating member on the first tube enables the oxygen-rich blood to partially pump out from the first tube through the first output port while a subsequent restoration of the second tube to its original shaft enables the second tube to suck in as much as pumped out therefrom through the second input port valve.

The advantages of the cardiopulmonary life support system according to the present invention are numerous. Initially, the gently alternating reciprocal movement of the alternating member squeezes the first and second tubes sequentially, alternately, gently and efficiently for blood pumping operation so that the oxygenator becomes less pressurized by the repeated blood pumping, thereby substantially decreasing incurrence of blood clotting (thrombosis) and dissolution or destruction of red blood cells (hemolysis), which are known as common side effects to most patients receiving assistance of conventional artificial hearts.

Further, the first and second tubes are formed of a flexible, resilient material and the solid alternating member is operatively provided between the first and second tubes in such a simplified, stabilized construction that the expected life span of the life support system is substantially extended without system replacement. In addition, the alternating member and the first and second tubes are efficiently accommodated within the housing to alternately enable each blood pumping operation for the first and second tube in such a limited space that a significant system size decrease is realized, for example, from a conventional refrigerator size to a palm size in an implantation version of the present invention or to a portable size in an extracorporeal assistance version of the present invention.

Also, the gentle, pulsatile blood pumping operation accomplished within the housing in systematic combination of the flexible blood tubes and the gently alternating solid member generates safe and steady blood pulses substantially similar to those of a natural heart, thereby improving product reliability. More importantly, the artificial blood pumping system adapting the alternately tube-squeezing mechanism requires less elements and further simplifies the overall structure for the blood pumping operation, thereby substantially decreasing production cost, whereby a surgical implantation of the life support system may be realized, for example, within about one and half times the medical bill charged for a large surgical heart operation.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE PREFERRED EMBODIMENTS

Figure 1:
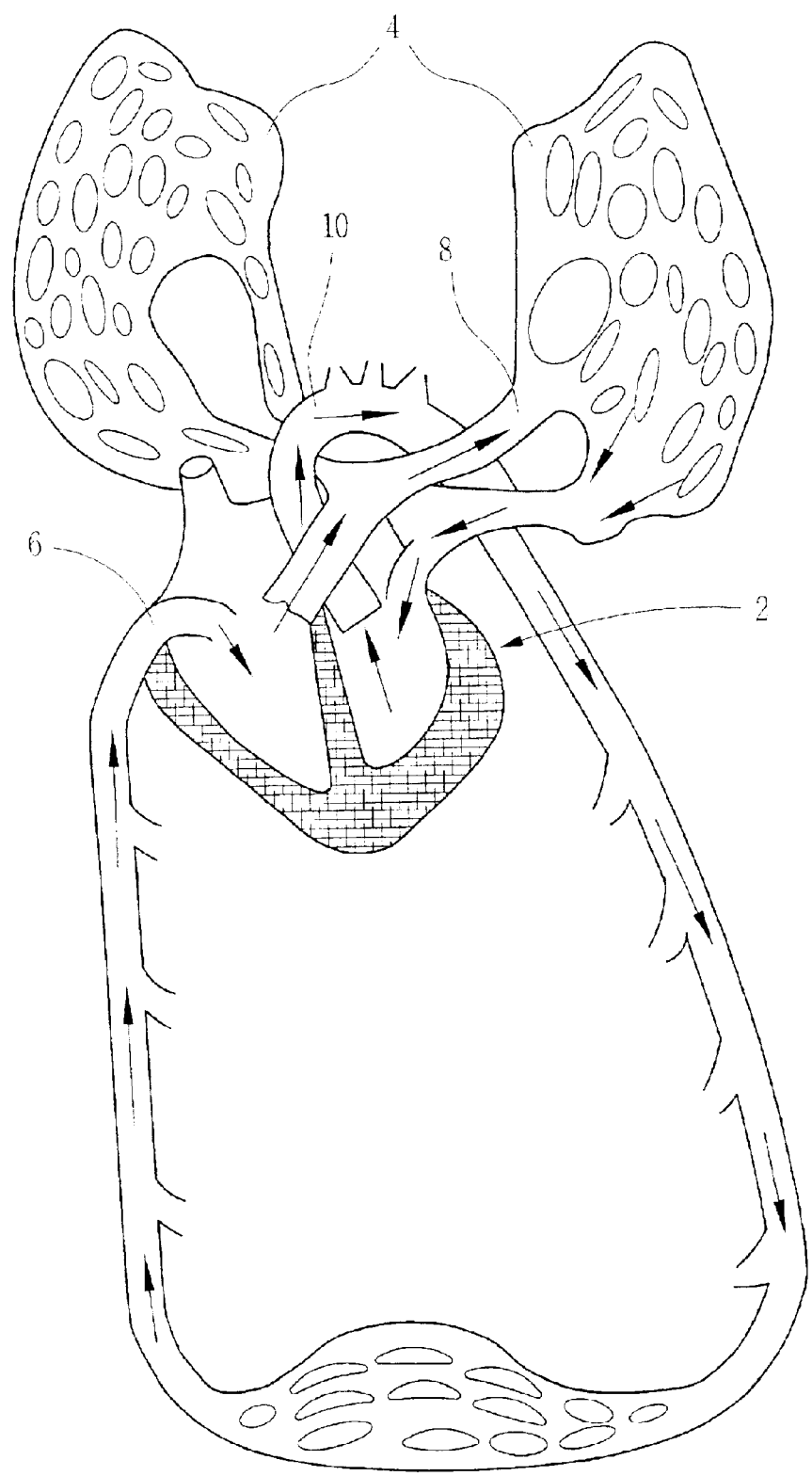
FIG. 1 is a schematic view showing a heart, lungs and a blood circulation in a mammal or a human.
Figure 2:
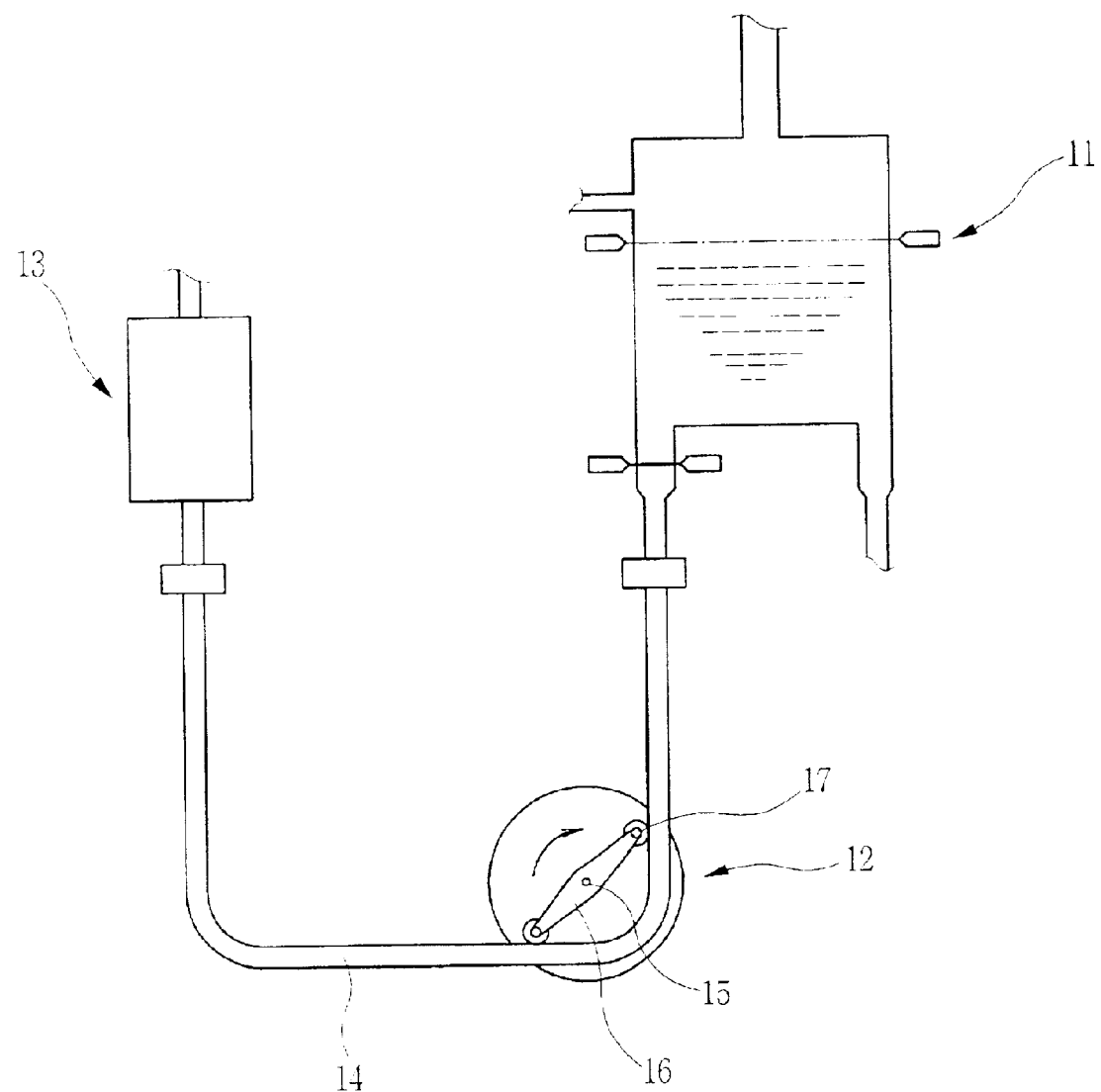
FIG. 2 is a structural view showing a conventional cardiopulmonary device using a rotary blood pump.
Figure 3:
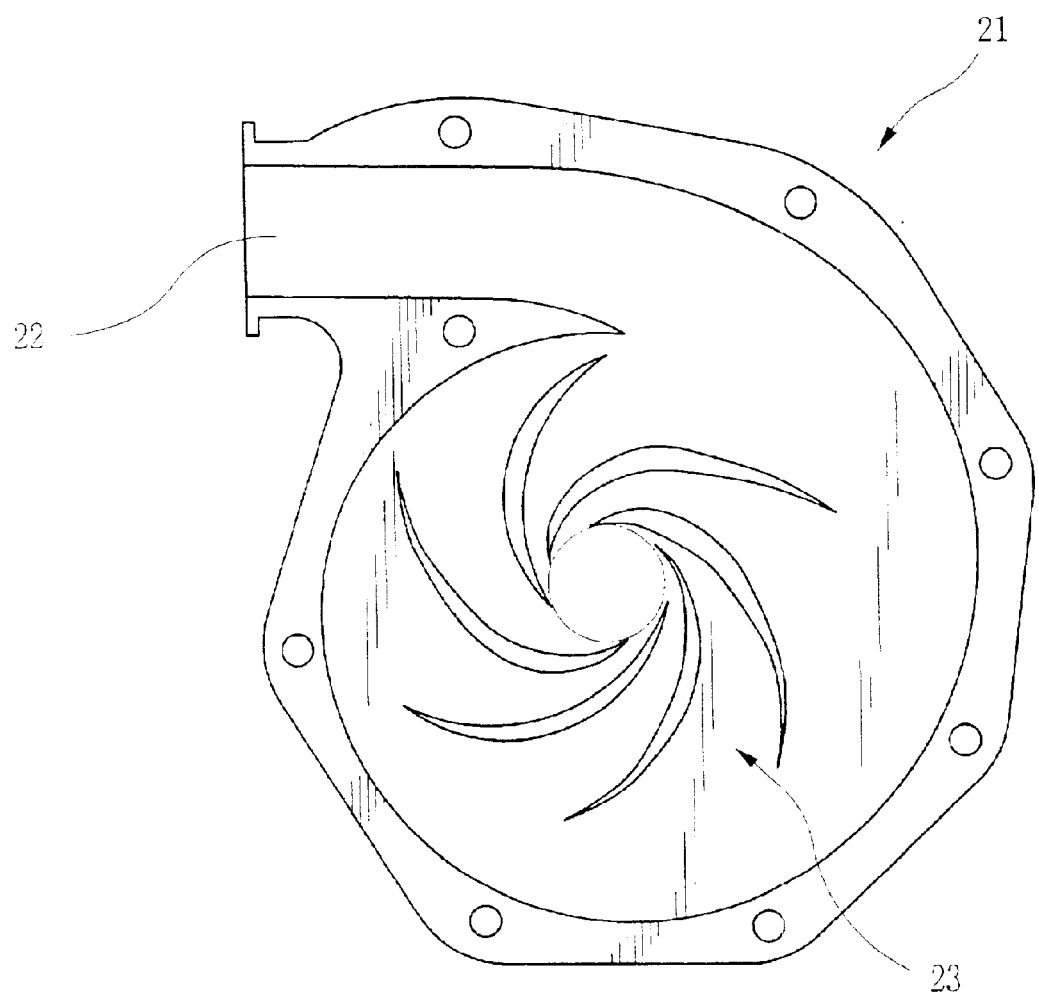
FIG. 3 is a schematic cross-sectional view of another conventional cardiopulmonary device using a centrifugal blood pump.
Figure 4:
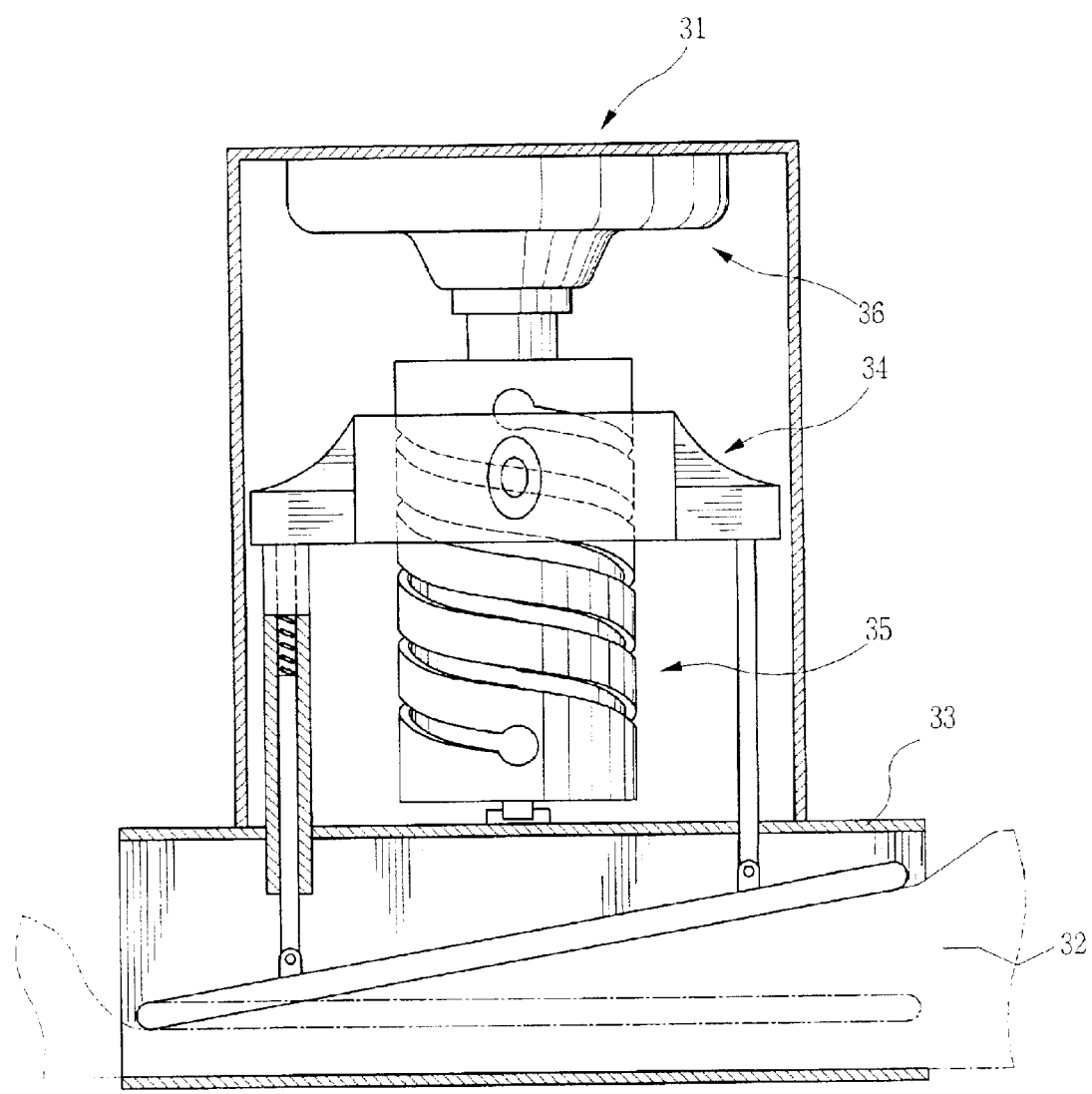
FIG. 4 is a structural view showing a further conventional cardiopulmonary device using a pulsatile blood pump.
Figure 5:
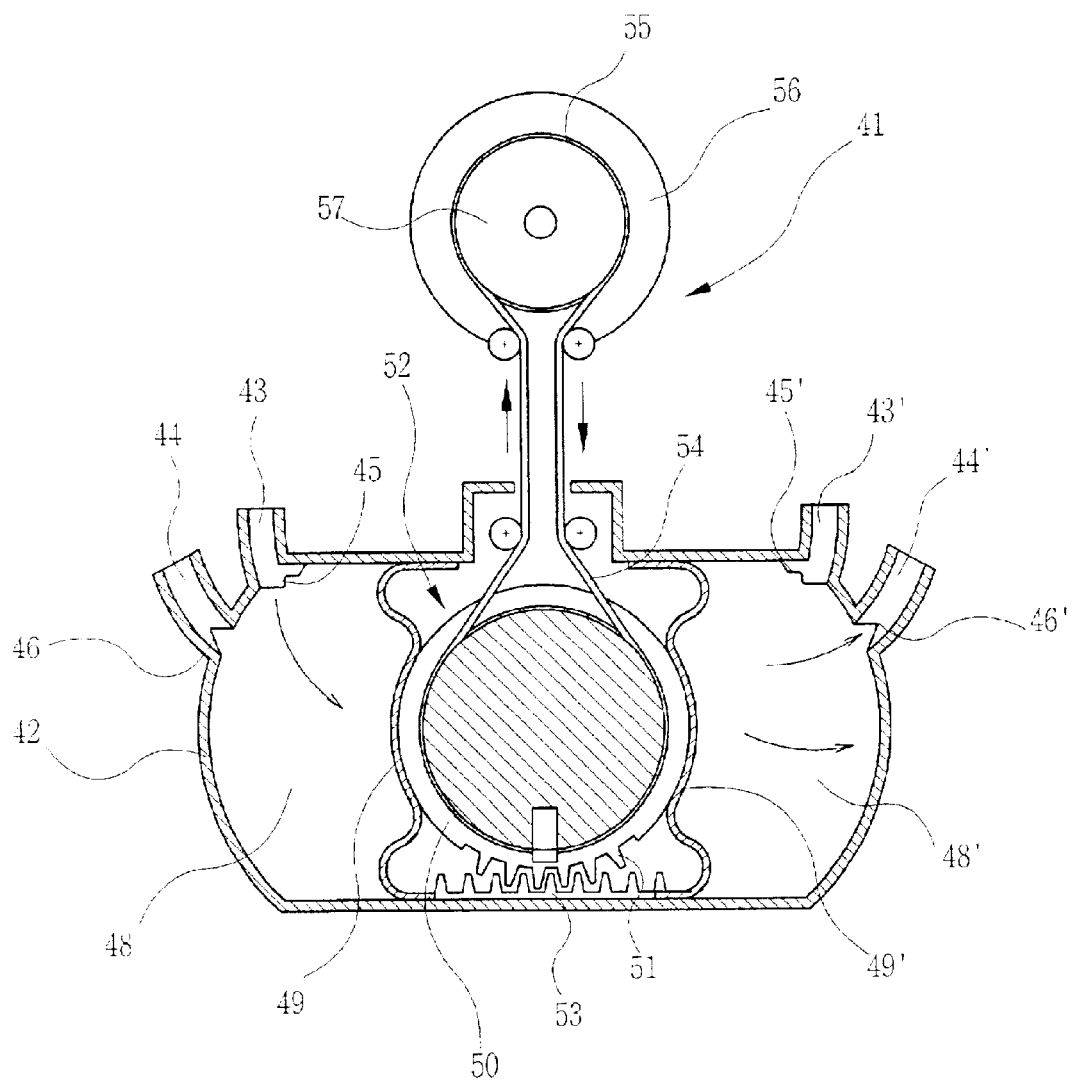
FIG. 5 is a cross-sectional view showing a still further conventional cardiopulmonary device using a dual pulsatile blood pump.
Figure 6:
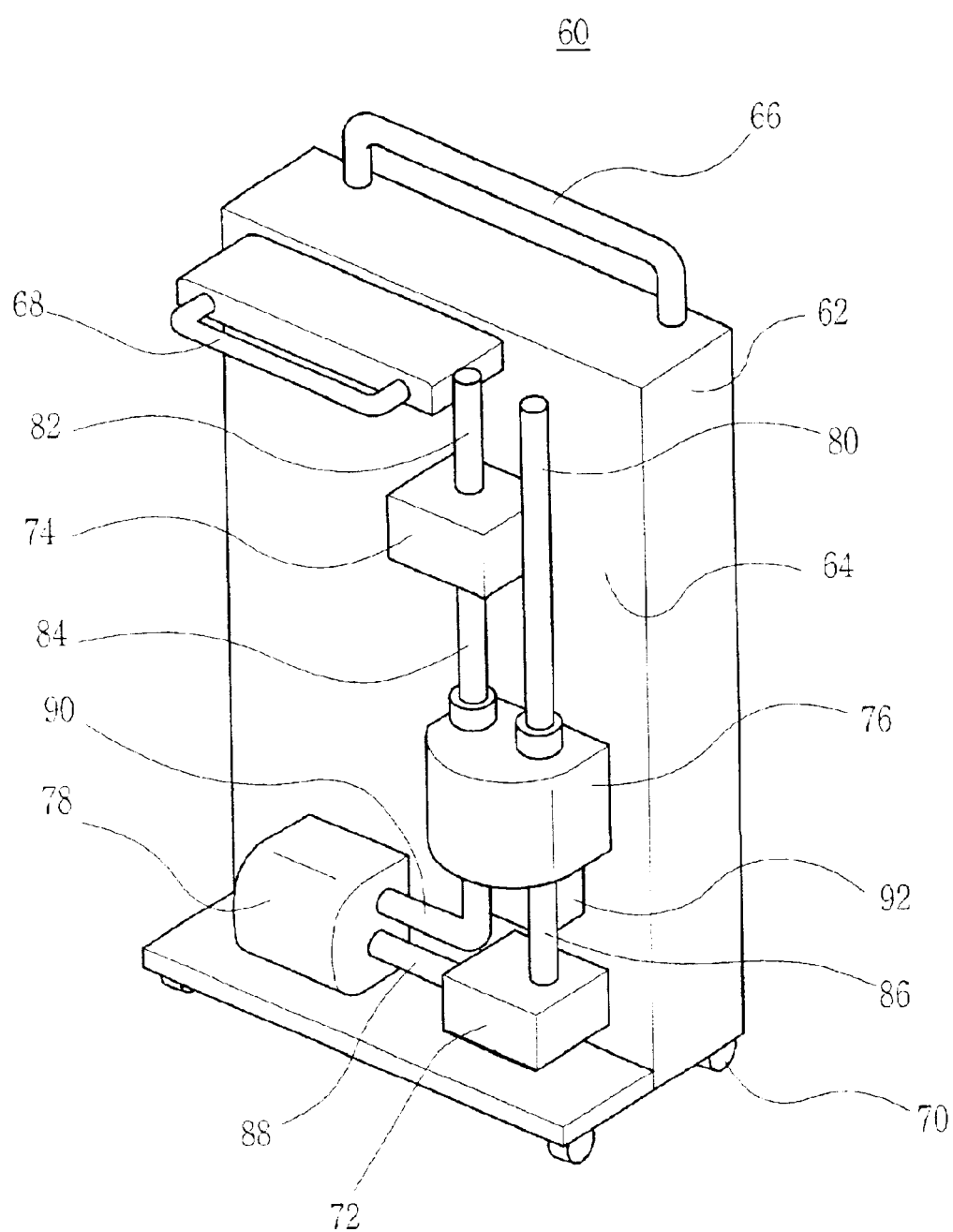
FIG. 6 is a perspective view showing a cardiopulmonary life support system according an embodiment of the present invention.
Figure 7:
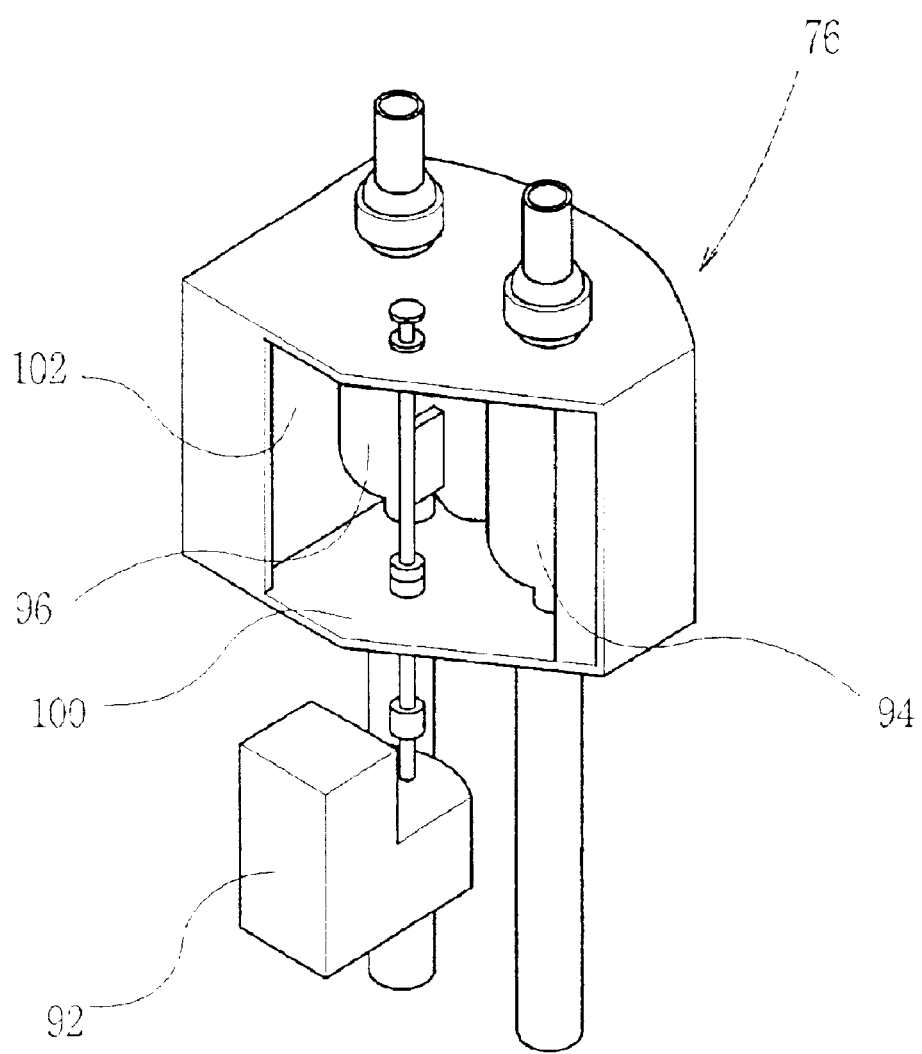
FIG. 7 is a perspective view detailing a blood pump unit in FIG. 6.

As shown in FIGS. 6 and 7, a cardiopulmonary life support system 60 according to an embodiment of present invention includes a support body 62 having a side wall 64. The support body 62 is selectively provided with handles 66, 68 and rollers 70 to facilitate portability and to improve mobility of the system 60. On the side wall 64 are attached first and second blood storages 72, 74, a blood pump housing 76, and an oxygenator 78, which are linked by ducts 80, 82, 84, 86, 88, 90. In this construction, a general blood stream is sequentially made through the duct 82 to be connected to a main vein of a patient, the second storage 74, the duct 84, the second tube 96 in the housing 76, the duct 90, the oxygenator 78, the duct 88, the first blood storage 72, the duct 86, the first tube 94 in the housing 94, and the duct 80 to be connected to an aorta of the patient. Here, each duct is formed of a flexible material to facilitate blood flowing therethrough.

To see a general arrangement of each element for the life support system 60, the first blood storage 72 is formed between the oxygenator 78 and the first tube 94 via the ducts 88, 86 to temporarily store therein an oxygen-rich blood oxygenated in the oxygenator 78. The second blood storage 74 is connected to the second tube 96 via the duct 84. The second storage 74 temporarily stores therein an oxygen-depleted blood that flows therein from the main vein via the duct 82.

When the life support system 60 is applied to a patient requiring an extracorporeal heart assistance, an oxygen-depleted blood flows in through the duct 82 that is to be connected to a main vein of the patient and is oxygenated in the oxygenator 78. In accordance with a pumping operation in the housing 76, the oxygenated, oxygen-rich blood flows out through the duct 80 that is to be connected to an aorta of the patient. The pumping operation in the housing 76 is driven by a motor unit 92 that is adjacent to the housing 76. The housing 76 is defined by a top side 98, a bottom side 100, and an inner periphery 102.

Figure 8:
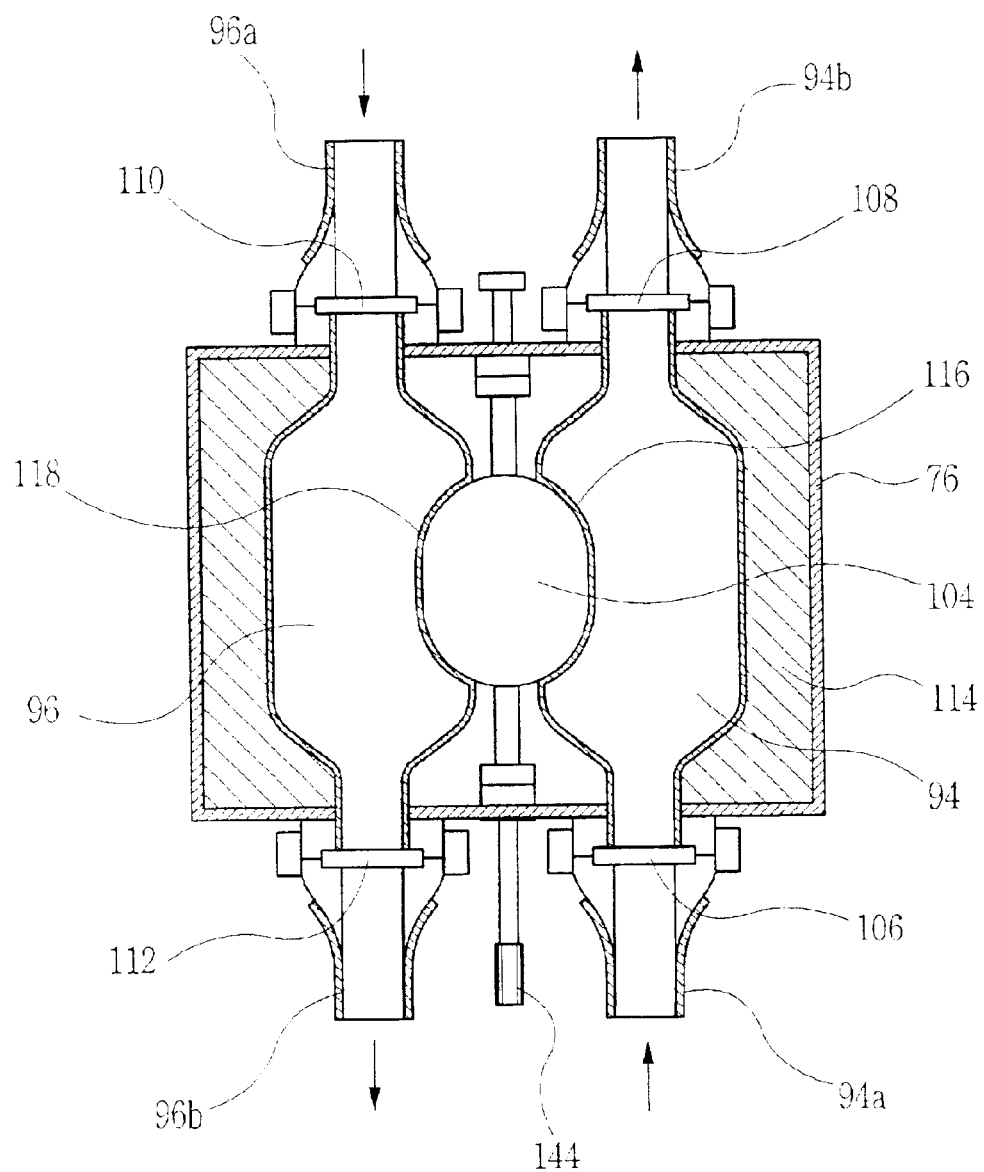
FIG. 8 is a cross-sectional front view of the blood pump unit in FIG. 6.
Figure 9:
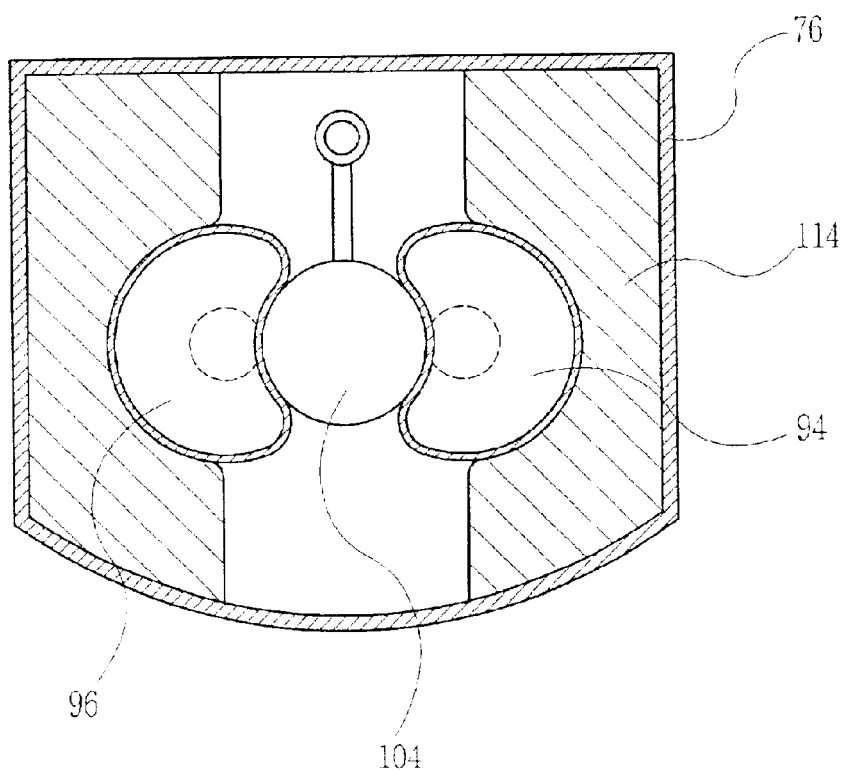
FIG. 9 is a cross-sectional top view of the blood pump unit in FIG. 6.
Figure 10:
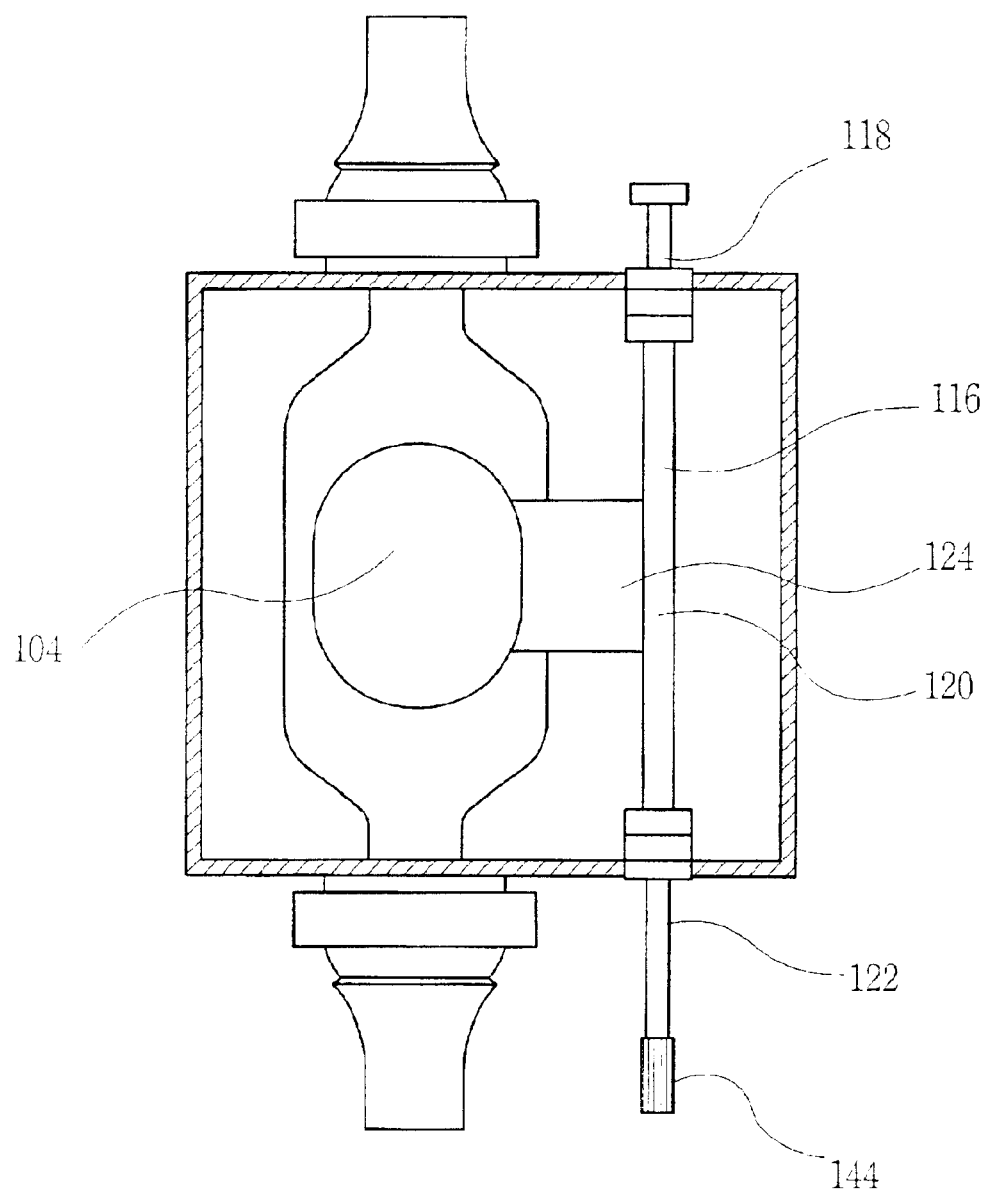
FIG. 10 is a cross-sectional side view of the blood pump unit in FIG. 6.

FIGS. 8, 9 and 10 specify construction of a blood pumping mechanism of the life support system 60. As shown therein, the first and second tubes 94, 96 are provided adjacent to each other in the housing 76. The first and second tubes 94, 96 each have an input port 94a, 96a and an output port 94b, 96b. An alternating member 104 is disposed between the tubes 94, 96 and attached to the housing 76 so as to alternately squeeze the first and second tubes 94, 96. That is, the alternating member 104 serves to partially thrust each tube 94, 96 in a sequential or an alternating order in accordance with the motor unit 92 to efficiently control a blood flow in and out of the first and second tubes 94, 96. Preferably, the alternating member 104 is solid in a spherical shape. The alternating member 104 may be also shaped in a capsule type with a solid formation. The first and second tubes 94, 96 are linearly aligned and substantially parallel with each other in the housing 78.

The life support system 60 further comprises valves 106, 108, 110, 112 each of which is a one-way valve to allow a single directional stream therethrough. The valves 106, 108, 110, 112 are sequentially formed in the input and output ports 94a, 94b, 96a, 96b to prevent a reverse stream in the first and second tubes 94, 96. So the blood flows into the first tube 94 through the first input port 94a in which the first input valve 106 that is a one-way valve disposed in the first input port 94a blocks the reverse stream from the first tube 94. Also, the blood in the first tube 94 may flow out through the first output port 94b in which the first output valve 108 that is a one way valve blocks a possible reverse stream from the duct 80 into the first tube 94. Likewise, the second input valve 110 in the second input port 96a prevents a reverse stream from the second tube 96 and the second output valve 112 in the second output port 96b serves to prevent a reverse stream from the duct 90 linked to the oxygenator 78 into the second tube 96.

In order to improve efficiency of the sequential pumping operation in the housing 76, the life support system 60 also includes a tube support 114 that is fitted between each tube 94, 96 and the inner periphery 102 of the housing 76. The tube support 114 is formed in a solid material and substantially spaced from the alternating member 104. At least, each tube portion 116, 118 that makes direct contacts with the alternating member 104 becomes protected from the tube support 114. Namely, the solid tube support 114 does not in the least prevent activation of the alternating member 104 but serves to stabilize the pumping operation in the housing 76 despite the flexible characteristic of each tube 94, 96. Selectively, the tube support 114 may be formed of either a substantially solid material or a substantially rigid material.

The first and second tubes 94, 96 are each formed of a flexible material. Further, each tube 94, 96 may be formed of a polymer known to well harmonize with a mammal body in terms of either a surgical operation or a bodily implantation. Selectively, the first and second tubes 94, 96 may be formed of silicon. According to such a material characteristic, the first and second tubes 94, 96 are each elastically, substantially restored to its original shape after being squeezed by the alternating member 104.

To improve usability of the life support system 60, the input port 96a for the second tube 96 and the output port 94b for the first tube 94 are each formed through the top side 98 of the housing 76. That is, the output port 94b of the first tube 94 passes through the top side 98 and the output port 96b of the second tube 96 passed through the bottom side 100 of the housing 76.

Importantly, the alternating member 104 serves to generate an artificial rhythmic pulsation substantially similar to the natural blood pumping in the heart of a living body. Specifically, an initial squeezing of the alternating member 104 on the first tube 94 enables a blood to partially pump out from the first tube 94 through the first tube output port 94b. A subsequent squeezing of the alternating member 104 on the second tube 96 enables the blood to partially pump out from the second tube 96 through the second tube output port 96b while a restoration of the first tube 94 to its original shape enables the first tube 94 to suck in as much as pumped out therefrom through the first input port valve 106. And, a further subsequent squeezing of the alternating member 104 on the first tube 94 enables the blood to partially pump out from the first tube 94 through the first tube output port 94b while a subsequent restoration of the second tube 96 to its original shaft enables the second tube 96 to suck in as much as pumped out therefrom through the second input port valve 110.

Figure 11:
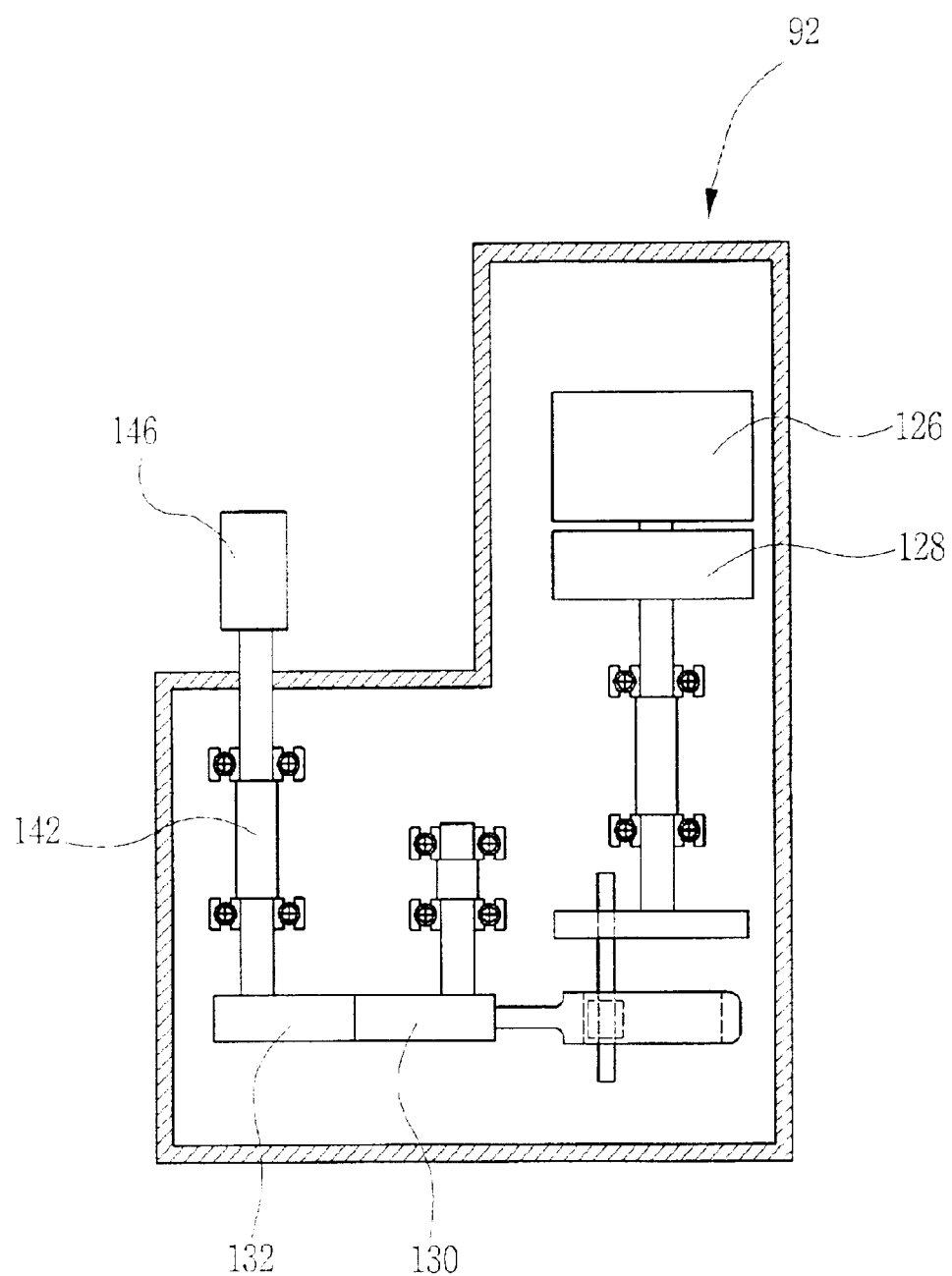
FIG. 11 is a schematic structural view of a pump drive unit in FIG. 6.
Figure 12:
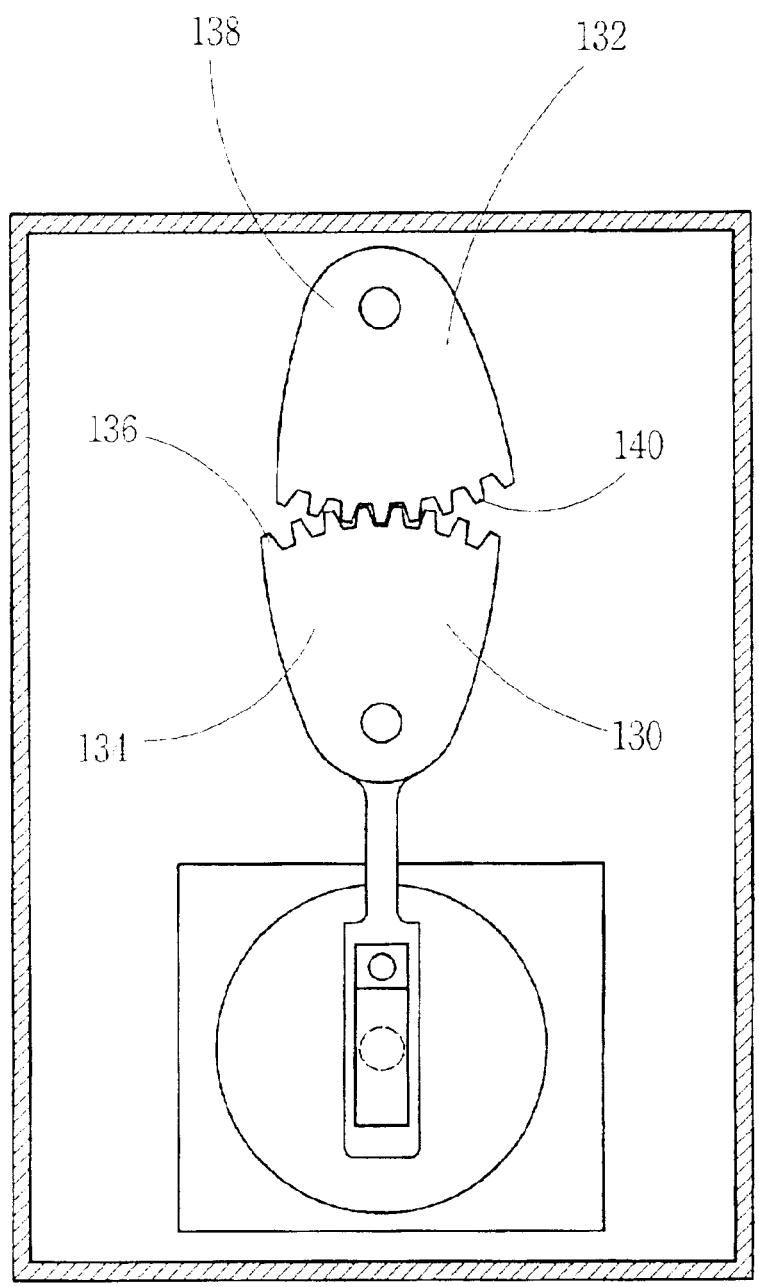
FIG. 12 is a top view of a link unit in FIG. 11.
Figure 13:
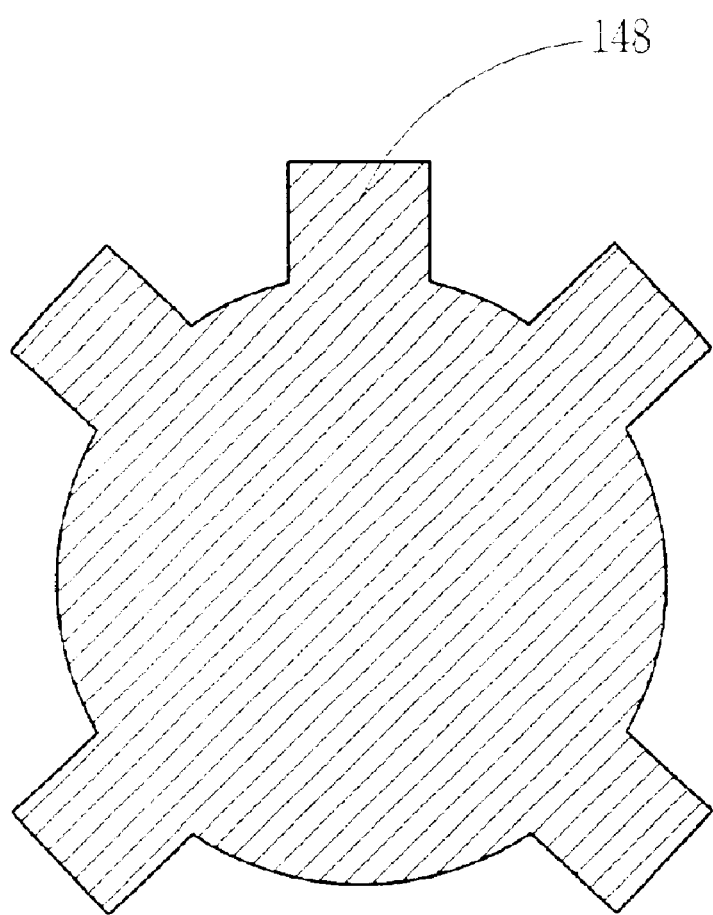
FIG. 13 is a cross-sectional view of a male spline in FIG. 6.

FIGS. 11, 12 and 13 each show a mechanism to actuate the alternating member 104. As shown therein, the life support system 60 further includes a shaft 116 having a top portion 118, a mid portion 120, and a bottom portion 122. The shaft 118 is connected to the motor unit 92 and substantially parallel to the tubes 94, 96. The top portion 118 of the shaft 116 is rotatably attached to the top side 98, the mid portion 120 is fixedly attached to the alternating member 104, and the bottom portion 122 rotatably passes through the bottom side 100 of the housing 76, whereby an angular reciprocal rotation of the shaft 116 enables the alternating member 104 to alternately squeeze the first and second tubes 94, 96.

As shown back in FIG. 10, a support plate 124 is formed between the alternating member 104 and the mid portion 120 of the shaft 116. That is, the support plate 124 extends from the mid portion 120 of the shaft 116 fixedly to the alternating member 104. In order to actuate the shaft 116, the motor unit 92 includes a motor 126, a decelerator 128, first and second gears 130, 132. The decelerator 126 is connected to the motor 126 to moderate a torque from the motor 126. The first gear 130 has a base 134 and gear teeth 136, and the second gear 132 has a base 138 and gear teeth 140. The first gear base 134 is connected to the decelerator 128, and the first gear teeth 136 is rotatably connected to the second gear teeth 140 of the second gear 132. A connecting rod 142 extends from the second gear base 138.

Meanwhile, male and female splines 144, 146 are detachably provided between the shaft 116 and the connecting rod 142. That is, the male spline 144 in FIG. 8 is attached to the bottom portion 122 of the shaft 116 and detachably engaged to the female spline 146, in FIG. 11. The female spline 146 is linked to the second gear base 132 via the connecting rod 142. So the rotational torque generated by the motor 126 and moderated by the decelerator 128 is converted to an angular reciprocal rotation in accordance with the first and second gears 130, 132. Specifically, the first and second gear teeth 136, 140 are each formed in an arc rack to enable generation of the angular reciprocal rotation. For a reliably detachable engagement between the male and female splines 144, 146, the matching teeth may be shaped in a safety formation as shown in FIG. 13. It is recommended that teeth 148 in each spline 144, 146 be formed in an irregular alignment.

Figure 14:
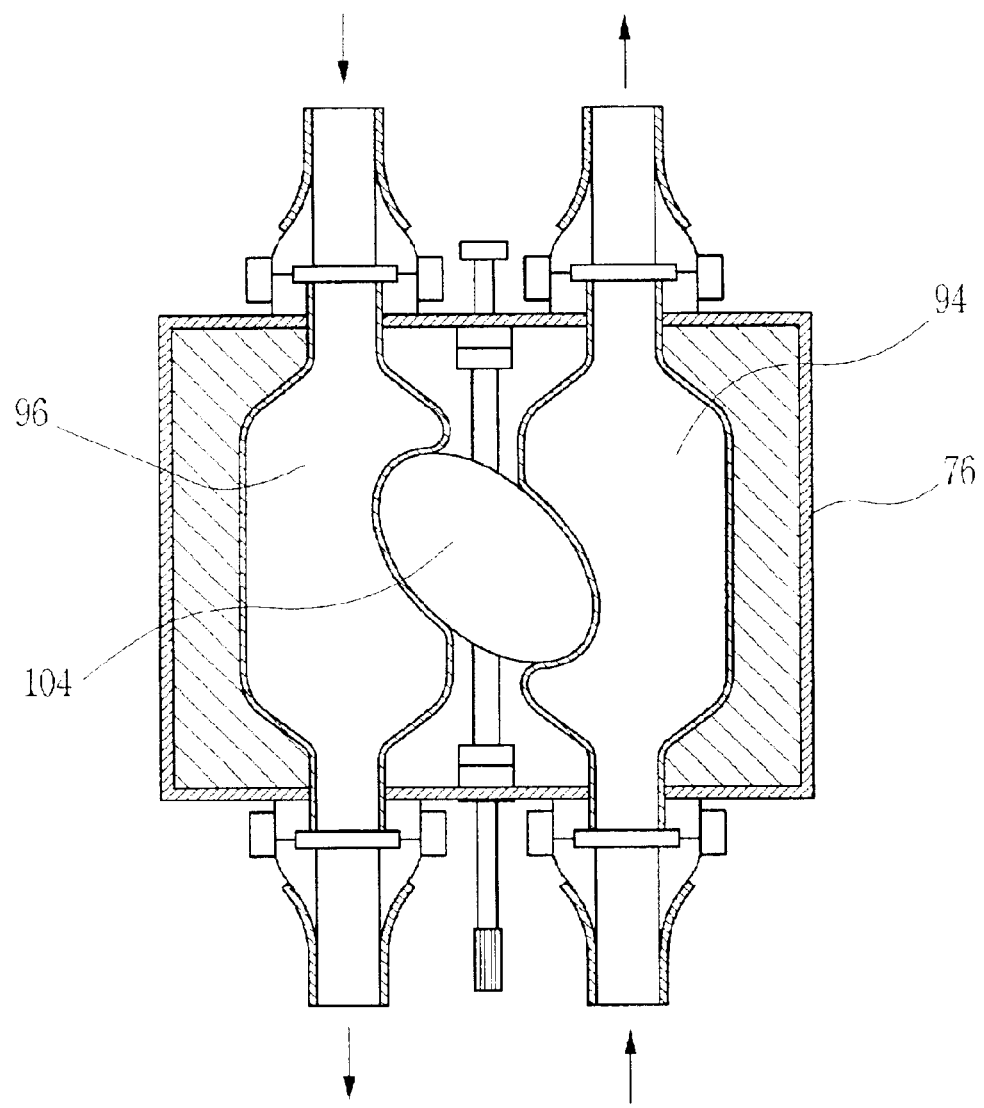
FIG. 14 is a cross-sectional front view of the blood pump unit in FIG. 6 according to another embodiment of the present invention.

The alternating movement of the alternating member 104 is preferably implemented in a horizontal direction between the first and second tubes 94, 96. The alternating member 104 may be provided in a slanting ellipsoid to realize an alternate diagonal squeezing on the first and second tubes 94, 96 as shown in FIG. 14.

Figure 15:
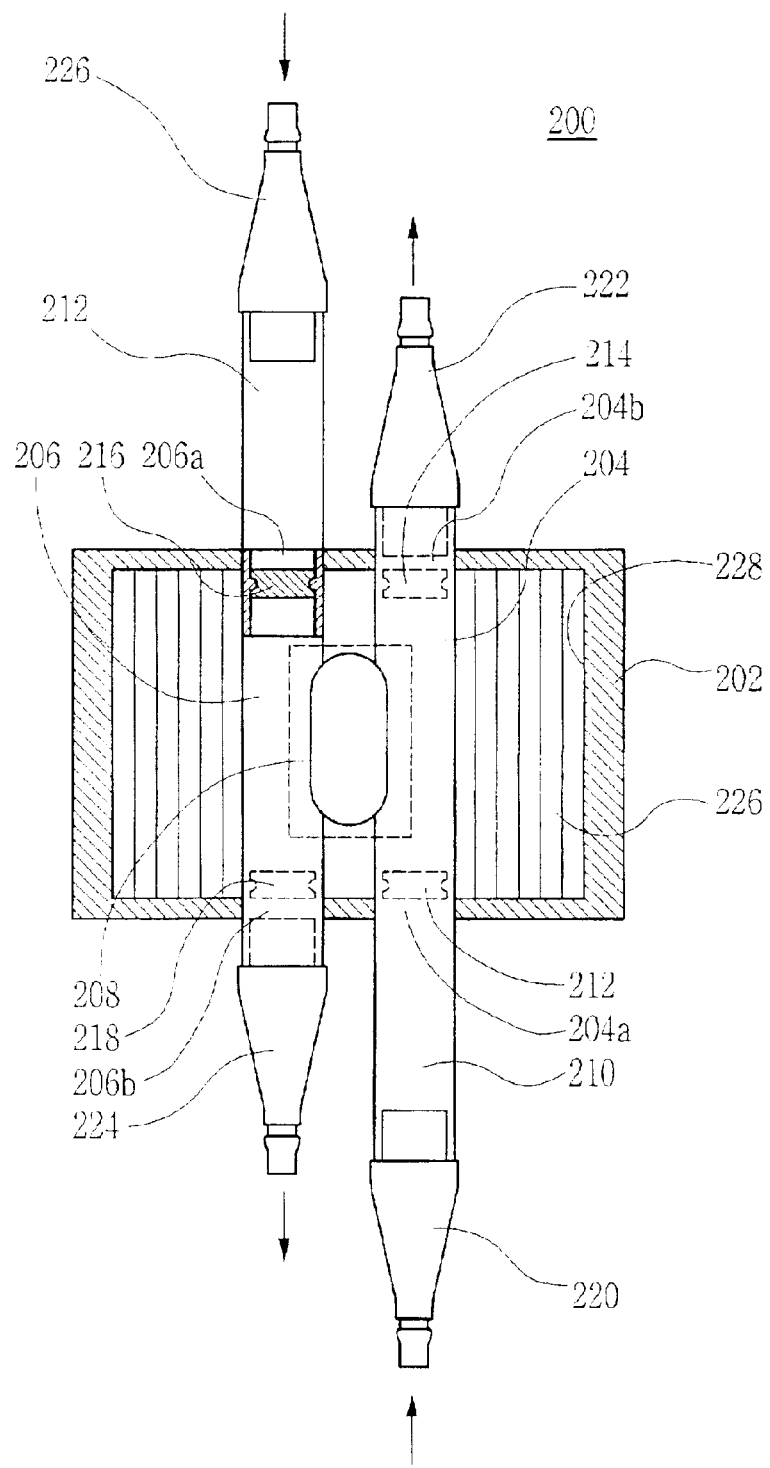
FIG. 15 is a structural view of a blood pump unit according to another embodiment of the present invention.
Figure 16:
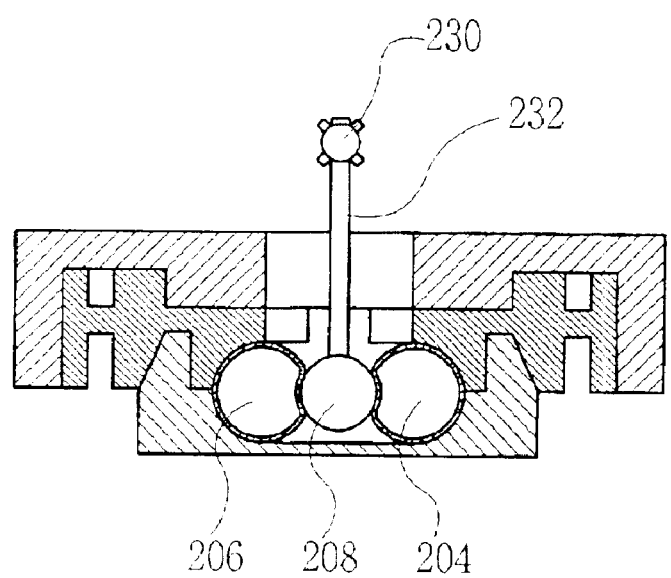
FIG. 16 is a cross-sectional top view of the blood pump unit in FIG. 15.

In FIGS. 15 and 16, a cardiopulmonary life support system 200 according to another embodiment of the present invention is provided in a decreased formation in size to fit for its surgical implantation. As shown therein, the life support system 200 includes a housing 202, first and second tubes 204, 206, an alternating member 208, a first blood storage 210, and a second blood storage 212. Each tube 204, 206 has input and output ports 204a, 204b, 206a, 206b each of which sequentially includes valves 212, 214, 216, 218 therein to allow a one-way stream in and out of the tubes 204, 206.

Also, the first blood storage 210 serves to temporarily store therein an oxygenated blood. The second blood storage 212 temporarily reserves therein an oxygen-depleted blood. Short ducts 220, 222, 224, 226 may be provided depending on requirements. A solid tube support 226 is formed between each tube 204, 206 and an inner periphery 228 of the housing 202 to stabilize the blood pumping operation in accordance with the alternating member 208 which is attached to a shaft 230 via an extension 232.

In this construction, the angular reciprocal rotation of the shaft 230 enables the alternating member 208 to alternately make a horizontal squeezing on the first and second tubes 204, 206. Accordingly, the first tube 204 regularly pumps out the oxygen-rich blood through the first output valve 214 into an aorta of a heart patient and concurrently the oxygen-depleted blood in the second tube 206 partially flows out through the second output valve 208 for blood oxygenation. Then, the oxygenated blood flows into the first tube 204 to wait for the squeezing of the alternating member 208.

The advantages of the cardiopulmonary life support system according to the present invention are numerous. First, the gently alternating reciprocal movement of the alternating member squeezes the first and second tubes sequentially, alternately, gently and efficiently for blood pumping operation so that the oxygenator becomes less pressurized by the repeated blood pumping, thereby substantially decreasing incurrence of blood clotting (thrombosis) and dissolution or destruction of red blood cells (hemolysis), which are known as common side effects to most patients receiving assistance of conventional artificial hearts.

Second, the first and second tubes are formed of a flexible, resilient material and the solid alternating member is operatively provided between the first and second tubes in such a simplified, stabilized construction that the expected life span of the life support system is substantially extended without system replacement.

Third, the alternating member and the first and second tubes are efficiently accommodated within the housing to alternately enable each blood pumping operation for the first and second tube in such a limited space that a significant system size decrease is realized, for example, from a conventional refrigerator size to a palm size in an implantation version of the present invention or to a portable size in an extracorporeal assistance version of the present invention.

Fourth, the gentle, pulsatile blood pumping operation accomplished within the housing in systematic combination of the flexible blood tubes and the gently alternating solid member generates safe and steady blood pulses substantially similar to those of a natural heart, thereby improving product reliability.

Fifth, the artificial blood pumping system adapting the alternately tube-squeezing mechanism requires less elements and further simplifies the overall structure for the blood pumping operation, thereby substantially decreasing production cost, whereby a surgical implantation of the life support system may be realized, for example, within about one and half times the medical bill charged for a large surgical heart operation.

Although the invention has been described in considerable detail with reference to certain preferred versions thereof, other versions are possible by converting the aforementioned construction. Therefore, the scope of the invention shall not be limited by the specification specified above and the appended claims.

What is claimed is:

1. A cardiopulmonary life support system comprising:
   a) a housing defined by a top side, a bottom, a rear side, and an inner periphery;
   b) first and second tubes adjacent to each other in the housing, wherein the first and second tubes each have an input port and an output port;
   c) an alternating member attached to the housing and disposed between the first and second tubes, wherein the alternating member alternately squeezes the first and second tubes;
   d) a valve formed in said each input and output port to prevent a reverse stream in the first and second tubes;
   e) a solid tube support fitted between said each tube and the inner periphery of the housing; and
   f) a shaft substantially parallel to the tubes, wherein the shaft has a top portion rotatably attached to the top side, a mid portion fixedly attached to the alternating member, and a bottom portion rotatably passing through the bottom side of the housing, whereby an angular reciprocal rotation of the shaft enables the alternating member to alternately squeeze the first and second tubes.

2. The life support system of claim 1 further comprising:
   a) a motor adjacent to the housing;
   b) a decelerator connected to the motor; and
   c) a first gear having a gear base connected to the decelerator, wherein the first gear is rotatably connected to the shaft.

3. The life support system of claim 2 further comprising a second gear having a gear base attached to the bottom portion of the shaft, wherein the second gear is rotatably engaged to the first gear.

4. The life support system of claim 3 wherein a male spline is fixed to the bottom portion of the shaft by a base thereof, and a female spline is fixed to the second gear base by a base thereof, wherein the male spline is detachable engaged to the female spline.

5. The life support system of claim 1 wherein a support plate extends from the mid portion of the shaft fixedly to the alternating member to stabilize the angular reciprocal rotation of the alternating member.

6. The life support system of claim 1 wherein the first and second tubes are linearly aligned substantially parallel with each other.

7. The life support system of claim 1 wherein the first and second tubes are each elastically, substantially restored to its original shape after being squeezed by the alternating member.

8. The life support system of claim 1 wherein said each valve is a one-way valve to allow a single directional stream therethrough.

9. The life support system of claim 1 wherein an initial squeezing of the alternating member on the first tube enables a blood to partially pump out from the first tube through the first tube output port, wherein a subsequent squeezing of the alternating member on the second tube enables the blood to partially pump out from the second tube through the second tube output port while a restoration of the first tube to its original shape enables the first tube to suck in as much as pumped out therefrom through the first input port valve, wherein a further subsequent squeezing of the alternating member on the first tube enables the blood to partially pump out from the first tube through the first tube output port while a subsequent restoration of the second tube to its original shaft enables the second tube to suck in as much as pumped out therefrom through the second input port valve.

10. The life support system of claim 1 wherein the output port of the first tube passes through the top side and the output port of the second tube passes through the bottom side of the housing.

11. A cardiopulmonary life support system comprising:
    a) a housing defined by a top side, a bottom, a rear side, and an inner periphery;
    b) first and second tubes adjacent to each other in the housing, wherein the first and second tubes each have an input port and an output port;
    c) an alternating member attached to the housing and disposed between the first and second tubes, wherein the alternating member alternately squeezes the first and second tubes;
    d) a valve formed in said each input and output port to prevent a reverse stream in the first and second tubes;
    e) an oxygenator connected to the output port of the first tube and the input port of the second tube to convert an oxygen-depleted blood to an oxygen-rich blood;
    f) a solid tube support fitted between said each tube and the inner periphery of the housing; and
    g) a shaft substantially parallel to the tubes, wherein the shaft has a top portion rotatably attached to the top side, a mid portion fixedly attached to the alternating member, and a bottom portion rotatably passing through the bottom side of the housing, whereby an angular reciprocal rotation of the shaft enables the alternating member to alternately squeeze the first and second tubes.

12. The life support system of claim 11 further comprising first and second blood storages, wherein the first blood storage is formed between the oxygenator and the input port of the first tube to temporarily store therein the oxygen-rich blood oxygenated in the oxygenator, wherein the second blood storage is connected to the output port of the second tube to temporarily store therein the oxygen-depleted blood.

13. The life support system of claim 12 wherein an initial squeezing of the alternating member on the first tube enables the oxygen-rich blood to partially pump out from the first tube through the first tube output port, wherein a subsequent squeezing of the alternating member on the second tube enables the oxygen-depleted blood to partially pump out from the second tube through the second output port while a restoration of the first tube to its original shape enables the first tube to suck in as much as pumped out therefrom through the first input port valve, wherein a further subsequent squeezing of the alternating member on the first tube enables the oxygen-rich blood to partially pump out from the first tube through the first output port while a subsequent restoration of the second tube to its original shaft enables the second tube to suck in as much as pumped out therefrom through the second input port valve.

14. The life support system of claim 11 further comprising:
a) a motor adjacent to the housing;
b) a decelerator connected to the motor; and
c) a first gear having a gear base connected to the decelerator, wherein the first gear is rotatably connected to the shaft.

15. The life support system of claim 14 further comprising a second gear having a gear base attached to the bottom portion of the shaft, wherein the second gear is rotatably engaged to the first gear.

16. The life support system of claim 15 wherein a male spline is fixed to the bottom portion of the shaft by a base thereof, and a female spline is fixed to the second gear base by a base thereof, wherein the male spline is detachably engaged to the female spline.

17. The life support system of claim 16 wherein a support plate extends from the mid portion of the shaft fixedly to the alternating member to stabilize the angular reciprocal rotation of the alternating member.

18. The life support system of claim 17 wherein the first and second tubes are linearly aligned substantially parallel with each other.

19. The life support system of claim 18 wherein the first and second tubes are each elastically restored to its original shape after being squeezed by the alternating member.

20. The life support system of claim 19 wherein said each valve is a one-way valve to allow a single directional stream therethrough.

21. The life support system of claim 20 wherein the output port of the first tube passes through the top side and the output port of the second tube passes through the bottom side of the housing.

* * * * *